United States Patent
Bedetti

(10) Patent No.: US 9,884,811 B2
(45) Date of Patent: Feb. 6, 2018

(54) FLUID BED GRANULATION OF UREA AND RELATED APPARATUS

(75) Inventor: Gianfranco Bedetti, Lugano-Besso (CH)

(73) Assignee: Casale SA, Lugano-Besso (CH)

(*) Notice: Subject to any disclaimer, the term of this patent is extended or adjusted under 35 U.S.C. 154(b) by 961 days.

(21) Appl. No.: 13/984,733

(22) PCT Filed: Dec. 6, 2011

(86) PCT No.: PCT/EP2011/071872
§ 371 (c)(1),
(2), (4) Date: Aug. 9, 2013

(87) PCT Pub. No.: WO2012/113473
PCT Pub. Date: Aug. 30, 2012

(65) Prior Publication Data
US 2013/0316078 A1  Nov. 28, 2013

(30) Foreign Application Priority Data
Feb. 21, 2011 (EP) .................................... 11155207

(51) Int. Cl.
C07C 273/02 (2006.01)
C05C 9/00 (2006.01)
C05G 3/00 (2006.01)

(52) U.S. Cl.
CPC ............ *C07C 273/02* (2013.01); *C05C 9/005* (2013.01); *C05G 3/0058* (2013.01)

(58) Field of Classification Search
None
See application file for complete search history.

(56) References Cited

U.S. PATENT DOCUMENTS

| 4,857,098 A | 8/1989 | Shirley, Jr. |
| 5,653,781 A | 8/1997 | Kayaert et al. |
| (Continued) | | |

FOREIGN PATENT DOCUMENTS

WO  2005/092486 A1  10/2005

OTHER PUBLICATIONS

International Search Report issued in connection with PCT/EP2011/071872.

(Continued)

*Primary Examiner* — Shamim Ahmed
*Assistant Examiner* — Bradford M Gates
(74) *Attorney, Agent, or Firm* — Akerman LLP

(57) ABSTRACT

A process for preparation of a granular urea product by granulating a urea solution in a fluidized bed, where the granulation process takes place along a substantially longitudinal growth path, from a granulation starting end ($1_S$) to a product discharge end ($1_E$) of said fluidized bed, and said urea solution enters the fluidized bed by means of several urea inputs ($2_A$, $2_B$, $2_C$) taken from a main urea feed (2), where an additive (6) is mixed with said urea solution said additive has a non-uniform concentration in said urea inputs, so that at least two of said urea inputs have a different concentration of additive.

7 Claims, 4 Drawing Sheets

(56) References Cited

U.S. PATENT DOCUMENTS

| | | | |
|---|---|---|---|
| 6,322,606 B1 | 11/2001 | Komoriya et al. | |
| 6,528,594 B1 * | 3/2003 | Bauer | C08J 3/122 |
| | | | 159/47.2 |
| 2007/0059446 A1 | 3/2007 | Mutsers | |
| 2010/0140827 A1 | 6/2010 | Bedetti | |
| 2010/0247507 A1 | 9/2010 | Harz et al. | |

OTHER PUBLICATIONS

International Preliminary Report on Patentability issued in connection with PCT/EP2011/071872.

* cited by examiner

FLUID BED GRANULATION OF UREA AND RELATED APPARATUS

This application is a national phase of PCT/EP2011/071872, filed Dec. 6, 2011, and claims priority to EP 11155207.1, filed Feb. 21, 2011, the entire contents of both of which are hereby incorporated by reference.

FIELD OF THE INVENTION

The present invention relates to a process and apparatus for fluid-bed granulation of urea.

PRIOR ART

Urea granulation process in a fluidized bed is known. The process involves that fine droplets of a urea solution with a high concentration, usually 96% or greater, are sprayed onto particles of a fluidized bed. The urea solution is also called the growth liquid of the fluidized bed. Small solid particles (typically less than 2 mm diameter) of the same or another substance, called seeds, are also fed to the fluid bed, to promote the granulation working as starting points for the progressive deposition of the growth liquid. The bed is then formed by the seeds and the growing granules of urea. Fluidization is usually achieved with air.

In a conventional process, the granules delivered by the fluid bed are screened and oversize and undersize granules are utilized as seed material, e.g. the undersize granules are directed back to the fluid bed and the oversize granules are crushed to produce further seed material. Further to the above, it is known in the art to add a suitable additive to the urea solution prior to feed said solution to the fluidized bed. A common additive is formaldehyde which is added as granulation additive, to reduce dust formation, stabilize the urea granules and improve storage properties. The demand of formaldehyde is usually about 0.4-0.5% wt (percentage in weight) of total urea.

U.S. Pat. No. 5,653,781 discloses a process for the production of urea granules from a melt or solution of urea by spraying the urea melt or solution, which also contains an additive, and where the undersize fraction of granules together with crushed oversize granules serve as seeds (or nuclei) to the granulation process.

A drawback of this technique is that it the amount of additive in the fluidized bed and then the additive content of the final product cannot be determined accurately. In fact, the full amount of additive is introduced in the fresh urea solution prior to entering the fluidized bed, which means that the concentration of additive in the sprayed liquid is substantially the same along the entire bed. Moreover, some of the additive returns into the fluidized bed with the seed material formed by the undersize granules and crushed oversize granules. Turning to the specific example of formaldehyde as additive, the need of a certain concentration of formaldehyde in the outer layer of the granules has determined in the prior art the adoption of the above cited amount of 0.4-0.5% wt which is relatively high and generates some concerns for agricultural use.

EP 2 077 147 discloses a process where a portion of the growth liquid is used to produce directly the seed material and solves the problem of additive entrained by screened granules.

SUMMARY OF THE INVENTION

The problem faced by the present invention is to provide a more effective addition of additive(s) to fluid-bed granulation of urea. Said problem is solved with a process for preparation of a granular urea product by granulating a urea solution in a fluidized bed, where the granulation process takes place along a substantially longitudinal growth path, from a granulation starting end to a product discharge end of said fluidized bed, and said urea solution enters the fluidized bed by means of several urea inputs taken from a main urea feed, the urea inputs being distributed along said longitudinal path, from a first urea input which is the closest to said granulation starting end, to a last urea input which is the closest to said product discharge end, and where an additive is mixed with said urea solution, the process being characterized in that the concentration of said additive in the urea inputs is non-uniform, so that at least two of said urea inputs have a different concentration of said additive.

According to an embodiment of the invention, the full amount of said additive, or at least a portion of said additive, is mixed with the main feed of the urea solution downstream of the first urea input. According to another embodiment, the full amount of said additive is mixed with the first urea input.

The additive may be divided into a plurality of additive streams. According to some embodiments, each additive stream is mixed directly with a respective urea input. The additive streams may have the same flow rate, or some or all additive streams may have a specific flow rate different from other additive stream(s).

The main feed of urea solution may be practically formed by one flow line or more flow lines in parallel. Said input flows preferably correspond to feeding sections of the fluidized bed. Each feeding section may receive one or more urea input flows, said urea inputs being directed for example to spraying or atomizing systems or nozzles. For example, according to some embodiments, each feeding section has a spraying nozzle or a plurality of spraying nozzles.

The additive can be mixed with the urea solution in a concentrated or distributed manner, according to several methods of carrying out the invention.

In a first embodiment, concentrated (or localized) addition is carried out by mixing the full amount of additive with the main urea feed, in a selected injection point downstream the first urea input. This means that the additive will enter the fluidized bed together with urea solution sprayed downstream the injection point, while the first urea input has no additive. According to another embodiment, the full amount of the additive is concentrated directly into one of the urea inputs, preferably the last urea input, and no additive is present in the other inputs. In all the above cases, a non-uniform concentration of additive is obtained in the inputs of urea.

According to further embodiments, the available amount of said additive is also divided in a plurality of additive streams, and each additive stream is strategically directed to a section of the fluidized bed, by mixing the additive with the main urea feed in a selected injection point, or more preferably by mixing the additive directly with urea inputs. For example, each additive stream can be mixed with a respective urea input. These last embodiments provide the best accuracy in determining the concentration of additive in the fluidized bed. The flow rate of additive streams may be the same or, even more preferably, each additive stream may have a specific flow rate thus giving a further degree of freedom in determining the concentration of additive in each urea input and consequently in the fluidized bed.

The additives are preferably in a liquid form such as aqueous solution. A preferred additive is formaldehyde, which can be added with urea-formaldehyde solution, also known as "ureaform" or "form urea".

The invention may involve the addition of one additive or more additives. In embodiments with two or more additives, each additive can be introduced according to concentrated-mixing or distributed-mixing embodiments as above disclosed. Further additives may be purposively added to different stages of the granulation process, in order to produce granules comprising layers having a different composition. An additive can be mixed with the urea solution near the product discharge end of the fluidized bed, namely where the granules are almost completely formed, to produce granules with a coating specifically comprising said additive. Or an additive can be mixed with the first urea input to have a maximum concentration of the additive in the core of the granules.

For example, sulphur (S) is added near the product discharge end of the fluidized bed to produce sulphur coated granules of urea for fertilization.

The process is preferably a once-through process where all the seeds of the granulation process are generated by converting a selected amount of fresh urea solution into solid urea granules or pastilles and no seed material is obtained by recycling granules after screening. Said amount of fresh urea solution is preferably a minor portion of the total urea solution. Eventually, the fresh urea solution directed to seeds or nuclei formation may receive additive(s) where appropriate. A once-through process has the further advantage that the concentration of additives in the final product is not influenced by the recycle of granulated product for use as seed material.

The seeds formed by solidification of urea solution can be in the form of small spherical granules or prills or pastilles, according to various embodiments of the invention. For example the seeds or nuclei are produced by depositing liquid drops on a cooled conveyor belt, obtaining solid pastilles with a suitable diameter; in another embodiment the seeds or nuclei are produced in a small vertical prilling tower.

In a further application the process of the invention is applied to standard urea prills previously formed e.g. in a prilling tower, for example urea prills generated in an industrial-size prilling tower; in another application the process of the invention is applied to granules of urea.

A vortex condition is preferably established in the fluid bed, by means of appropriate feeding of a fluidizing medium, usually air. The vortex condition of the fluid bed can be realized with a transversal vortex or a double transversal vortex arrangement, meaning that the vortex has an axis substantially parallel to a main flow direction of the fluid bed. Details of a preferred vortex condition are described in WO 02/083320.

The main advantage of the invention is the ability to control the addition of the additive or, as the case may be, of more additives, in a more accurate way than prior art techniques. An additive can be injected strategically in a selected point or more selected points along the growth path of the fluidized bed, meaning that different stages of the granulation process can be carried out with different and controlled concentration of a certain additive; different additives can be added in different location to obtain desired structure or features of the final product. For example a desired concentration of an additive can be achieved in the zones of the fluidized bed where granulation starts around the nuclei, or a desired concentration of the same or another additive can be achieved near the outlet of the fluidized bed to produce a desired coating layer of the granules. For example, an advantage of the invention is the ability to concentrate an additive in the external layer of the granules, which allows to produce coated granules using a lower quantity of said additive, compared to the prior art where the additive is mixed with the urea melt prior to entering the bed.

As regards the addition of formaldehyde, it has been noted that the invention gives a good stabilization and storage properties with 0.2% wt or less formaldehyde. This is a significant advantage over the prior art since the cost of ureaform is relevant and the content of formaldehyde in granules of urea for agricultural use is an environmental concern.

Further to this, the invention gives ample freedom to change the composition of the granules. In particular, the invention may produce granules virtually with any composition of additives, thanks to the precise dosing of concentration of additives in the fresh urea solution, at different stages of the growth process.

A granulated urea product obtainable with the inventive process has for example a core portion and at least two layers containing an additive, a first inner layer having a content of said additive, and a second outer layer having a different content of the same additive. Said additive can be formurea, i.e. the invention allows obtaining granules with a non-uniform distribution of formurea, for example with more formurea in the outer part and less formurea in the inner part closer to the seed (or core) portion. Eventually, the granules have further layers with further additives.

A further aspect of the invention is an apparatus adapted to carry out the above process. The apparatus comprises a granulator and means for feeding the urea solution, including a main urea feed and urea input flow lines corresponding to the above urea inputs, and feeding means of said additive which are arranged to provide a non uniform concentration of the additive in the urea inputs.

In some embodiments, the additive feeding means comprising an additive line for injecting the full amount of said additive, or at least a portion of said additive, into the main feed of the urea solution downstream of the first urea input line, or for injecting the full amount of additive into a selected one urea input. In other embodiments, the additive feeding means comprising additive lines for mixing the additive directly with respective urea input lines taken from the main urea feed and directed to respective spraying means of the granulator.

Further characteristics and the advantages of the invention will be better elucidated with the help of the following description of illustrative and non limiting embodiments.

DETAILED DESCRIPTION OF PREFERRED EMBODIMENTS

Figure 1:
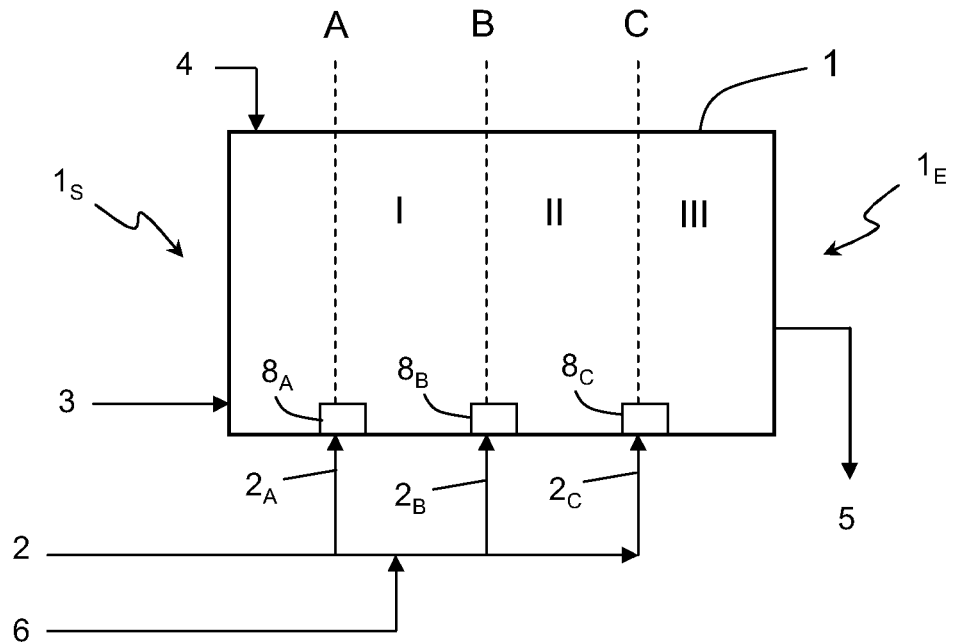
FIG. 1 is a scheme of a first embodiment of the process with concentrated addition of one additive to the urea solution.

Referring to FIG. 1, the block 1 designates a fluidized-bed granulator which receives a main feed 2 of urea solution and a fluidizing medium 3, usually air.

Line 4 indicates for example an input of solid seeds or nuclei which serve as starting points for the granulation process.

In use, a fluidized-bed is established inside said granulator 1. The granulation process takes place along a substantially longitudinal growth path, from a granulation starting end $1_S$ to a product discharge end $1_E$ of the granulator 1. The granulator 1 delivers a flow 5 of granulated urea.

The urea solution enters the granulator 1 by means of several urea inputs such as inputs $2_A$, $2_B$ and $2_C$ taken from a main urea feed 2. The urea inputs are distributed along said longitudinal path, from the first urea input $2_A$ which is the closest to the granulation starting end $1_B$, to a last urea input $2_C$ which is closest to the product discharge end $1_E$. In the example, each urea input $2_A$ to $2_C$ is directed to a respective spraying nozzle $8_A$-$8_C$. Reference $8_A$ to $8_C$ may denote spraying nozzles or respective arrays of spray nozzles.

Line 6 indicates a feed of an additive to be mixed the urea solution. In the embodiment of FIG. 1, the full amount of additive is mixed with the main feed 2 of urea, at an injection point downstream the first input $2_A$, i.e. downstream the first spraying nozzle $8_A$. Hence, a non-uniform concentration of additive in the urea inputs is obtained, since the additive is mixed with the solution of inputs $2_B$ and $2_C$ while absent in the first input $2_A$. Consequently, the additive is found in zones II and III of the fluidized bed, which means that a first granulation stage is carried out in the zone I substantially in absence of the additive of line 6.

It can be understood that granules of urea in this case will have substantially no additive in a core portion formed in the first zone I, and a substantially constant concentration of additive in an outer portion formed during the passage through zones II and III.

A variant of this embodiment provides that the amount of additive in flow line 6 is split into two or more parts and said parts are injected at selected points of the main urea feed 2, e.g. a first amount of additive is injected downstream the first input $2_A$ and a second amount of additive is injected downstream the second input $2_B$. Hence a different amount of additive in the inputs $2_B$, $2_C$ can be obtained.

Figure 2:
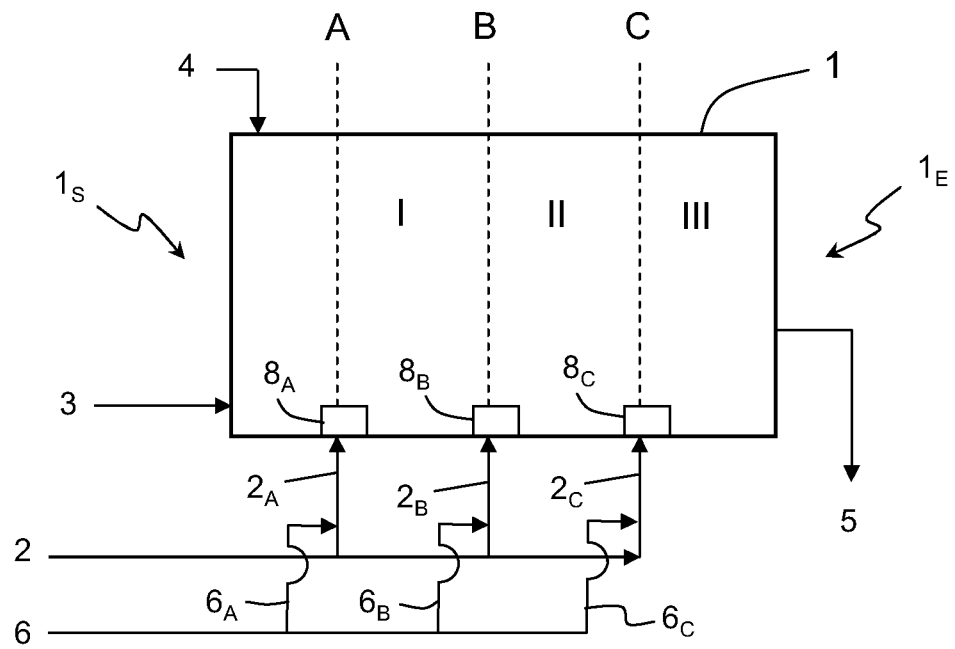
FIG. 2 is a scheme of a second embodiment of the process with distributed addition the additive.

FIG. 2 discloses another embodiment where the additive flow line 6 is divided into several flow lines $6_A$, $6_B$, $6_C$, and each additive flow line is mixed directly with a respective urea input $2_A$, $2_B$ and $2_C$. In this embodiment, no additive is mixed with the main feed 2 and concentration of the additive in the urea inputs $2_A$, $2_B$ and $2_C$ can be precisely controlled. To this purpose, the flow rate of each additive line $6_A$ to $6_C$ can be controlled by suitable (not shown) valves. As a consequence, also the concentration of additive in the zones I, II and III is independent and can be controlled with accuracy. A non-uniform concentration is obtained for example with a peak of concentration of the additive in any of inputs $2_A$, $2_B$ or $2_C$ and corresponding zones I, II or III.

Figure 3:
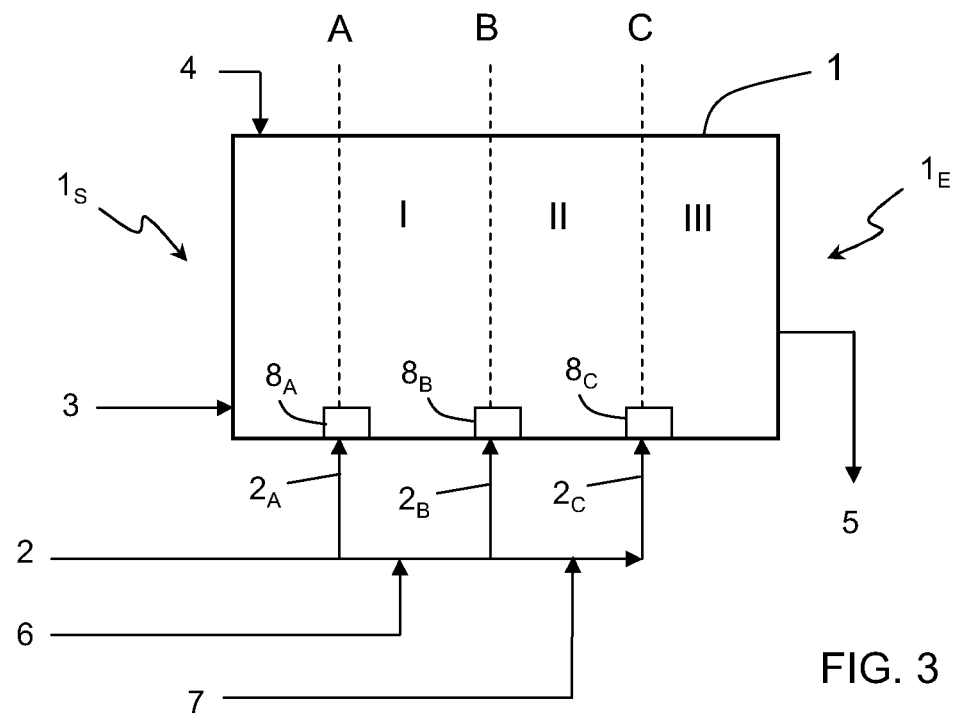
FIG. 3 is a scheme of a third embodiment of the process with addition of two different additives.

FIG. 3 discloses an embodiment with two additive flow lines 6 and 7, where the first line 6 carries a first additive, and the second line 7 carries a second additive. In the example, the first additive of line 6 is added to the main urea feed 2 downstream of the first input $2_A$ which means that some of said first additive is contained in the urea inputs $2_B$ and $2_C$ and zones II and III; the second additive of line 7 is added to the main urea feed 2 downstream of the second urea feed stream $2_B$, which means that the second additive, together with the first additive, is introduced with urea input $2_C$ into the zone III of the fluidized bed.

In some embodiments, the concentration of additive from the first input to the last input may be varied according to a monotonic law, e.g. having a minimum (or maximum) concentration in first input $2_A$, intermediate concentration in input $2_B$ and maximum (minimum) concentration of additive in input $2_C$.

Figure 4:
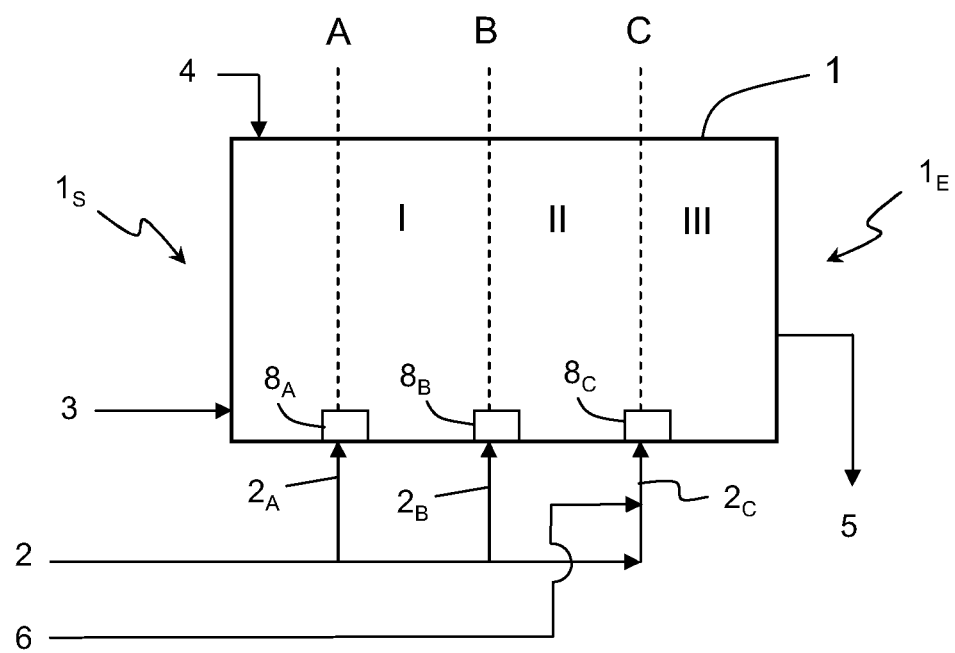
FIG. 4 is a scheme of a granule of urea obtainable with the invention.

FIG. 4 is another embodiment where the full amount of additive in flow line 6 enters the granulator 1 mixed with one urea input, namely the last urea input $2_C$. In this case a non-uniform input is obtained because no additive is found in previous inputs $2_A$ and $2_B$. This means that the additive will be concentrated in the outer layer portion of granules formed in zone III, while substantially absent in the core formed in portions I and II.

It shall be noted that any of the above embodiments can be combined or mixed. For example a portion of an additive can be mixed with the main urea feed, as seen for example in FIG. 1, and (an)other portion(s) can be mixed with any of the secondary flows of urea taken from the main feed and directed to the various feeding sections.

It shall be noted that the figures are for indicative purpose. The main urea feed 2 is schematic and the urea solution may be introduced for example with two main feeding lines at right and left sides of the granulator 1, or more.

In multiple-additive embodiments, each additive may be fed according to any of the embodiments of the invention, e.g. in a concentrated way as seen in FIGS. 1 and 3, or in a distributed way as in FIG. 2. For example a first additive can be introduced with the distributed embodiment of FIG. 2, and a second additive can be introduced with a concentrated embodiment such as additive 7 in FIG. 3. Introducing an additive close to the product discharge end $1_E$ has the advantage that a coating layer comprising said second additive is formed in the last stages of the granulation process.

Figure 7:
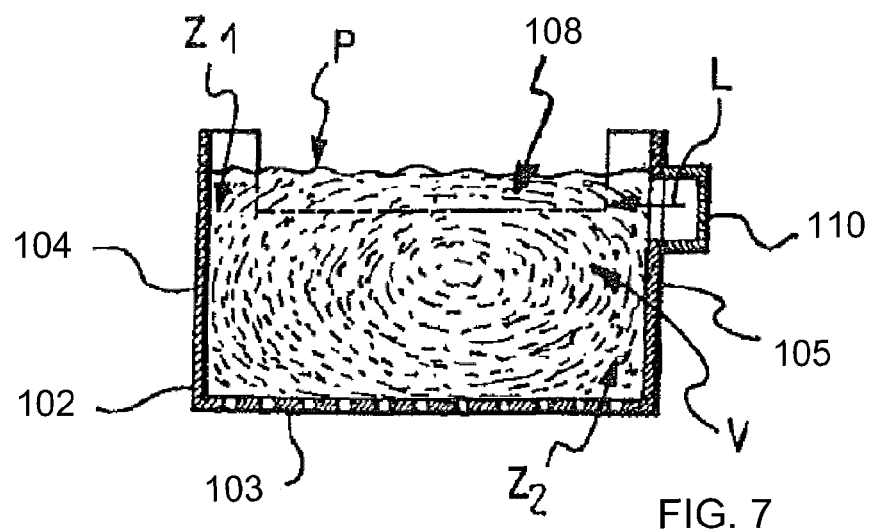
FIG. 7 is cross sectional views of the granulator according to a single-vortex embodiment.

A feature of the invention is the ability to produce layered granules which cannot be obtained with a conventional process. For example, FIG. 7 shows a granule of urea that can be formed by the process of FIG. 3. The granule comprises a core 60 formed by the nucleus or seed; a first layer 61 formed in the zone I where substantially no additive is present; a second layer 62 formed in the zone II comprising an amount of additive from line 6, namely the amount introduced via line $2_B$; a third coating layer 63 formed in the zone III and comprising the second additive of line 7 introduced via line $2_C$.

Figure 9:
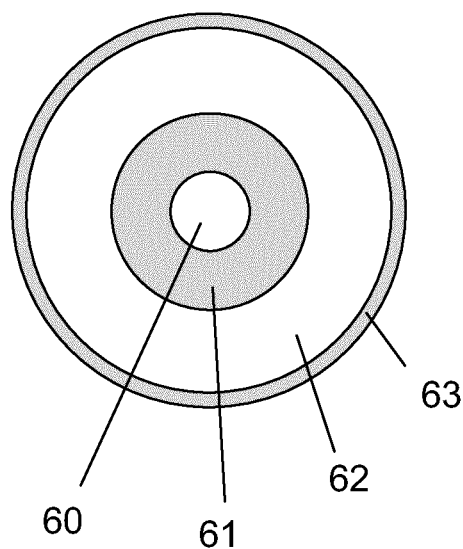
FIG. 9 is a section of a multi-layered granule obtainable with the invention.
Figure 5:
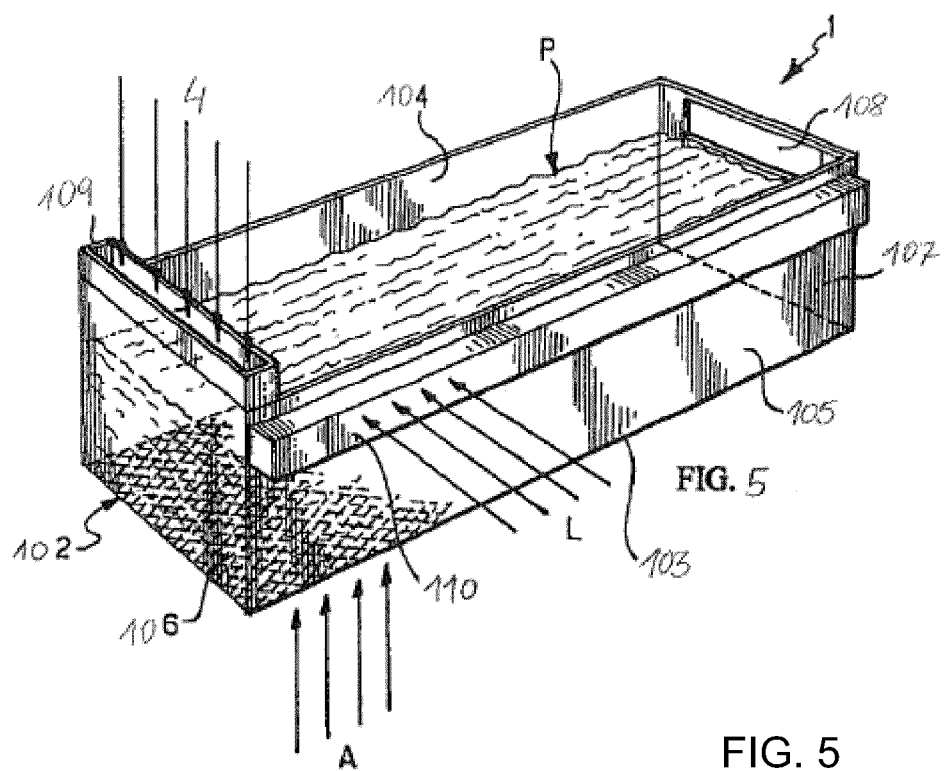
FIG. 5 is a perspective and simplified view of a granulator that can be used to carry out the invention.
Figure 6:
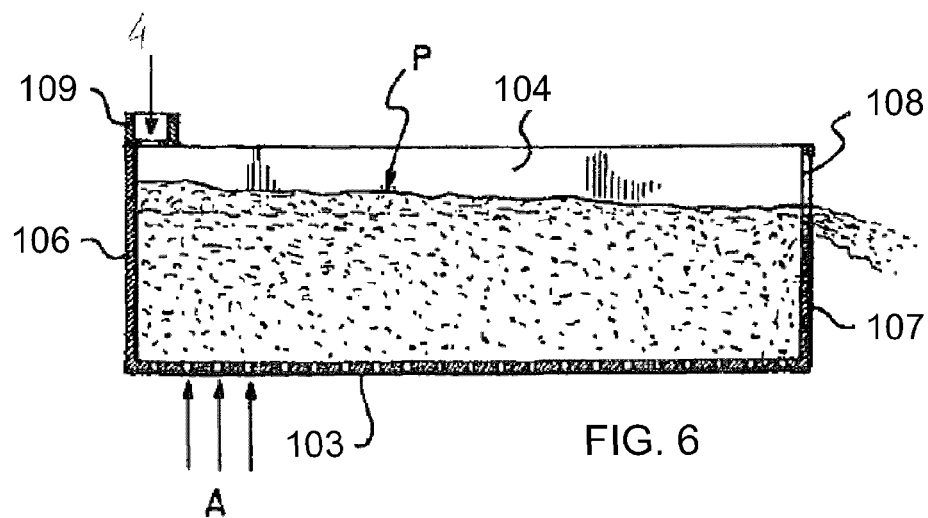
FIG. 6 is a longitudinal section of the granulator of FIG. 5.

In a preferred embodiment the additive of line 6 is a solution of urea containing formaldehyde (ureaform). For example this solution is about 60% formaldehyde, 20% urea and 20% water. A line 7 arranged as in FIG. 3 may add sulphur to produce sulphur-coated granular urea. Referring again to FIG. 9, it can be seen that layers 61, 62 and 63 may also have a different concentration of formurea.

The seeds of the granulation process are produced preferably by solidification of an amount of a fresh urea solution, preferably having the same composition of the urea solution of charge 2 but eventually including an additive. Said seeds or nuclei are produced in a suitable device, not shown. The seeds are e.g. spheres having a diameter of about 0.5 mm.

Embodiments of said device for seed generation include, for example, a cooled belt fed with a rotary former, or a compact prilling tower.

According to another embodiment of the invention, the flow line 4 carries standard urea prills produced in a prilling tower. Standard urea prills are larger than seeds and have generally a size (diameter) of about 1.5 to 2.5 mm. The flow 4 may also carry granules having a size larger than prills and generally a size (diameter) greater 2.5 mm.

The granulator 1 and the arrangement of the fluidized bed are now described with reference to a preferred embodiment of FIGS. 5 to 8. The fluid bed granulator 1 comprises a horizontal container 102 with a gas-permeable bottom part 103, for example made of a perforated element, two side walls 104, 105; a head wall 106 and a discharge wall 107.

The discharge wall 107 has a top opening 108 for discharging the granulated product and fixing the maximum height of the fluid bed. Other appropriate discharge means may be used such as for example an automatic valve operated by the fluid bed level.

A feeder 109 is installed at the upper side of the head wall 106, receiving the seeds o nuclei 4 and providing uniform distribution of the seeds along the head wall 106. A blowing system (not shown) is installed below the container 102, producing an air flow A to maintain the fluid-bed state of particulate material, comprising seeds and granules, inside the container 102, as well as a continuous vortex having a substantially horizontal axis. To this purpose, bottom part 103 of the container is perforated and is preferably provided with suitable conventional means for obtaining a non-homogeneous distribution of the air flow. This may happen for example by fractioning said flow A in fractions having different rates or by varying the entry direction of the air flow in the fluid bed. In addition, the seeds can be preheated by the air flow A.

The continuous discharge through opening 108 is counterbalanced by the continuous feeding of seeds S1 and determines a longitudinal main flow or fluid vein of the fluid bed, from head wall 106 towards the opposite wall 107. The free surface P is slightly inclined in the direction of the flowing bed as illustrated. It can be appreciated that the growth process takes place in a growth path from left to right of the figure, i.e. from the region near the head wall 106 to the region near the end wall 107.

The urea solution (growth liquid) is atomized and mixed with air and is introduced in container 2 via a side distributor 110, slightly below the free surface P of the fluid bed. Said distributor 110 extends along the whole length of container 102, providing a continuous and distributed supply of the atomized urea solution, corresponding to the feeding line 2 as schematized in FIGS. 1 to 3. The additives are suitably added via dedicated feeding lines in one or more injection points to the distributor 110.

Figure 8:
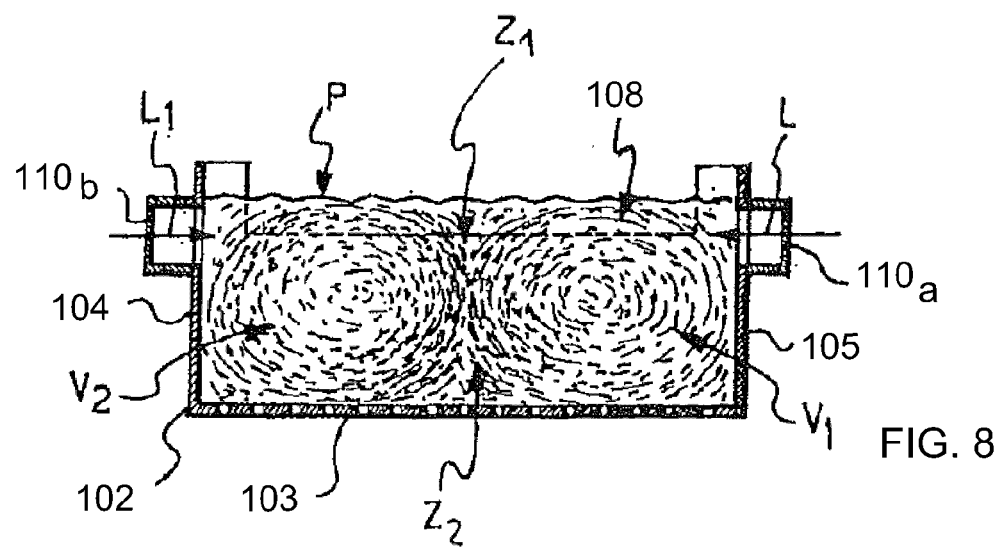
FIG. 8 is a cross sectional views of the granulator according to a double-vortex embodiment.

A continuous vortex V is preferably formed and maintained in the fluid bed as depicted in the cross section of FIG. 7. Said vortex V is transversal, i.e. with axis substantially parallel to the length of the container 102 and, hence, to the direction of the main flow (fluid vein) through the fluid bed. In a further embodiment, a double vortex $V_1$, $V_2$ is generated by spraying the urea solution with distributors 110a, 110b on both sides of the container 102 as shown in FIG. 8.

In use, the level of the fluid bed is determined by the discharge through opening 108 or an automatic discharge valve, following the main flow from head wall 106 towards the opposite wall 107. The fluid-bed particles (granules or seeds) located in the upper layer of the fluid bed are hit and wetted many times with the particles of atomized growth liquid of flow L, with solidification of the substance and partial evaporation of the solvent that may be inside said growth liquid. As a consequence, temperature of the granules is increased in the relative (upper) zone of the fluid bed.

The "wetted" granules are pushed towards the opposite wall 104 and deflect naturally towards the bottom 103 of the container 102, under the action of vortex V. In the course towards bottom 103, the granules leave the upper hot layer of the fluid bed crossing progressively colder layers. During this course the growth liquid is solidified and consolidated on the surface of the granules. This step is completed during the course of the granules, towards the wall 105; then the granules deflect near the wall 105 and again towards the upper hot layer of the fluid bed. The course described above is substantially repeated and the steps of wetting, solidification and evaporation are repeated with progressive mass and volume increase, during the path from wall 106 to wall 107 induced by the fluid vein. Wetting zones are denoted with $Z_1$ (FIGS. 7, 8) and solidification zones are denoted with $Z_2$.

The invention claimed is:

1. A process for preparation of a granular urea product by granulating a urea solution in a fluidized bed, where the granulation process takes place along a substantially longitudinal growth path, from a granulation starting end to a product discharge end of said fluidized bed, and said urea solution enters the fluidized bed by means of several urea inputs taken from a main urea feed, the urea inputs being distributed along said longitudinal path, from a first urea input which is the closest to said granulation starting end, to a last urea input which is the closest to said product discharge end, and where an additive is mixed with said urea solution, wherein the concentration of said additive in said urea inputs is non-uniform, so that at least two of said urea inputs have a different concentration of said additive, the process comprising:
dividing the additive into a plurality of additive streams, and mixing each additive stream directly with a respective urea input.

2. The process according to claim 1, wherein said additive streams have the same flow rate, or some or all additive streams have a specific flow rate different from other additive stream(s).

3. The process according to claim 1, wherein more than one additive is added to the urea solution, each additive having a dedicated flow line.

4. The process according to claim 3, wherein at least two additives are mixed with urea solution and mixed with the same or different urea input or urea inputs.

5. The process according to claim 1, wherein said additive or one of the additive streams is formaldehyde or a solution containing formaldehyde.

6. The process according to claim 1, the process being a once-through process where all the seeds of the granulation process are generated by converting an amount of fresh urea solution, optionally with an additive or additives, into solid urea granules or pastilles.

7. An apparatus for fluidized-bed granulation of a urea solution, comprising:
a granulator having a main longitudinal direction from a feed end where granulation is started to a product discharge end where urea granular product is discharged by the granulator,
a feeding means of the urea solution, comprising at least a main feed line and several urea input lines taken from said main feed line, and distributed along said longitudinal direction, from a first urea input which is the closest to said feed end, to a last urea input which is the closest to said product discharge end, the apparatus further comprising feeding means of an additive, wherein said feeding means of said additive are arranged to provide a non uniform concentration of the additive in the urea input flows, and in that the additive feeding means comprise additive lines for mixing the additive directly with respective urea input lines taken from the main urea feed and directed to respective spraying means of the granulator.

* * * * *